United States Patent
Lee et al.

(10) Patent No.: US 9,046,450 B2
(45) Date of Patent: Jun. 2, 2015

(54) COUPON GEOMETRIES THAT INDUCE FAILURE IN GAUGE AREA OF COMPOSITE FATIGUE TEST COUPONS

(71) Applicant: The Boeing Company, Chicago, IL (US)

(72) Inventors: Mitchell J. Lee, Scottsdale, AZ (US); Nicklaus Cummings Kimball, Mesa, AZ (US)

(73) Assignee: The Boeing Company, Chicago, IL (US)

( * ) Notice: Subject to any disclaimer, the term of this patent is extended or adjusted under 35 U.S.C. 154(b) by 12 days.

(21) Appl. No.: 13/769,485

(22) Filed: Feb. 18, 2013

(65) Prior Publication Data

US 2014/0234571 A1 Aug. 21, 2014

(51) Int. Cl.
*G01N 3/02* (2006.01)
*G01N 3/08* (2006.01)
*G01N 3/60* (2006.01)

(52) U.S. Cl.
CPC .. *G01N 3/02* (2013.01); *G01N 3/08* (2013.01); *G01N 3/60* (2013.01); *G01N 2203/0073* (2013.01)

(58) Field of Classification Search
CPC .............. G01N 2033/0003; G01N 2203/0073; G01N 2203/0067; G01N 3/08; G01N 2291/0258; G01N 3/02; G01N 3/20; G01N 2203/0017; G01N 3/10; G01N 3/12; G01N 3/14; G01N 3/16; G01N 3/165; G01N 3/18; G01B 2203/0005; Y10T 428/2918
USPC ........................................ 428/80; 73/760–860
See application file for complete search history.

(56) References Cited

U.S. PATENT DOCUMENTS 5,284,063 A 2/1994 Newell
7,798,014 B2 9/2010 Ferguson et al.

*Primary Examiner* — Aaron Austin
*Assistant Examiner* — Jasper Saberi
(74) *Attorney, Agent, or Firm* — Ostrager Chong Flaherty & Broitman P.C.

(57) ABSTRACT

A coupon geometry that reliably fails in the gauge area of the coupon during fatigue testing. The propensity to fail at the gauge area is imparted by using a bow-tie-shaped coupon coupled with similarly shaped tabs. The test coupons have a bow-tie-shaped profile with tapered sides that converge as they extend from the opposing ends of the coupon to the gauge area, forming a pair of trapezoidal portions (one the mirror image of the other) connected by the gauge area. These trapezoidal portions of the test coupon include the regions where similarly trapezoidal tabs will be adhered to the front and back of the coupon. The test coupon has a minimum width in the gauge area and a constant thickness, and a height of the gauge area is no greater than 3% of a height of the test coupon.

6 Claims, 3 Drawing Sheets

COUPON GEOMETRIES THAT INDUCE FAILURE IN GAUGE AREA OF COMPOSITE FATIGUE TEST COUPONS

FEDERALLY SPONSORED RESEARCH OR DEVELOPMENT

This invention was made with Government support under Contract No. W58RGZ-09-C-0161 awarded by the Department of Defense. The Government has certain rights in this invention.

BACKGROUND

This disclosure generally relates to geometries for test coupons used in material testing.

In materials science, fatigue is the progressive and localized structural damage that occurs when a material is subjected to cyclic loading, i.e., repeated loading and unloading. If the loads are above a certain threshold, microscopic cracks will begin to form at stress concentrators. Eventually a crack will reach a critical size, and the structure will fracture. Because the shape of the structure contributes to macro-level stress concentrations, it significantly affects the fatigue life of the material.

With the recent and rapid adoption of composite materials in aerospace structures, composite material testing has drawn ample attention and scrutiny. Fatigue testing of composite coupons is of particular interest, as a satisfactory test method for accurately determining a composite's fatigue behavior, often in the form of establishing a material's stress versus cycles to failure (S-N) curve, has yet to be established. Current composite fatigue specimens typically fail due to interactions with the test machine, thereby introducing error into the test results.

More specifically, current fatigue testing of composite coupons often results in premature failures in the vicinity of the test frame to coupon interface (which area is commonly referred to as the "grips"). This produces noisy, and in some cases unusable, fatigue data that at times has a tenuous relationship with actual material behavior. Part life, geometry, thickness, etc. may all be subsequently affected by the suspect fatigue data. Moreover, advanced coupon testing of damaged or repaired composite specimens (e.g., scratches, holes, patches) requires the damage or repair to be placed at the failure location of the pristine coupon. Without reliable failure in the gauge area, it is not possible to compare the damaged or repaired specimens to their pristine counterparts; thus, strength degradation factors cannot be established.

Per ASTM D3039, the current approach to test composite coupons in fatigue is to use rectangular coupons with rectangular tabs adhered on either end. This coupon shape is used for both static and fatigue tests. However, as conceded in Section 6.3 of ASTM D3479 (entitled "Standard Test Method for Tension-Tension Fatigue of Polymer Matrix Composite Materials"), which covers fatigue testing of composite coupons: "Premature failure of the specimen in the tab region is common in tension-tension fatigue testing as a result of stress concentrations in the vicinity of [the] tab region." The current coupon geometry for fatigue testing has no propensity to fail at the gauge section as the only stress concentrations occur in the vicinity of the tabs—either underneath the tab-to-grip interface or along the end of the tab, where the load is transferred completely to the composite. While this has limited detrimental effects in static testing, in fatigue testing failure near the tabs results in a majority of the fatigue specimens failing prematurely due to interactions with the test machine. This is especially pronounced in testing glass composite coupons.

There is a need for test coupon geometries that induce failure in the gauge area of composite test coupons.

SUMMARY

The subject matter disclosed herein is a coupon geometry that reliably fails in the gauge area of the coupon during fatigue testing, yielding high quality, relevant data about the desired composite material properties. The propensity to fail at the gauge area is imparted by using a bow-tie-shaped coupon coupled with similarly shaped tabs. In this disclosure, the term "similar" will be used in its geometric sense, to wit, two geometrical objects are called similar if they both have the same shape. If two objects are similar, each is congruent to the result of a uniform scaling of the other.

The subject test coupons are made of composite material and are designed to induce failure in a central section designated herein as the gauge area. These test coupons have a bow-tie-shaped profile with tapered sides that converge as they extend from the opposing ends of the coupon to the gauge area, forming a pair of trapezoidal portions (one the mirror image of the other) connected by the gauge area. These trapezoidal portions of the test coupon include the regions where similarly trapezoidal tabs will be adhered to the front and rear faces of the coupon.

One aspect of the subject matter disclosed in more detail hereinafter is a composite test coupon comprising: a first trapezoidal portion having first and second straight tapered sides; a second trapezoidal portion having third and fourth straight tapered sides; and a gauge area disposed between and connected to the first and second trapezoidal portions and having first and second radiused sides, the first radiused side being connected to the first and third straight tapered sides, and the second radiused side being connected to the second and fourth straight tapered sides, wherein the test coupon has a minimum width in the gauge area and a constant thickness, and a height of the gauge area is no greater than 3% of a height of the test coupon (measured from one end of the coupon to the other end).

In accordance with one embodiment, the first and second straight tapered sides diverge from each other and the third and fourth straight tapered sides diverge from each other as the first through fourth straight tapered sides extend away from the gauge area. The taper angles of the first through fourth straight tapered sides may be equal. The taper angle may be in a range of 1 to 10 degrees inclusive. Also the radii of the first and second radiused sides may be equal. The first and third straight tapered sides may be tangent to the first radiused side of the gauge area, and the second and fourth straight tapered sides may be tangent to the second radiused side of the gauge area.

Another aspect is a composite test coupon having a constant thickness, a height along a vertical axis, and a bow-tie-shaped profile when viewed along an axis in a thickness direction, wherein the bow-tie-shaped profile comprises left and right sides and top and bottom ends, the left side comprising a first radiused portion and first and third straight tapered portions extending from the first radiused portion toward the top and bottom ends respectively, and the right side comprising a second radiused portion and second and fourth straight tapered portions extending from the second radiused portion toward the top and bottom ends respectively. The first and second straight tapered portions extend from the first and second radiused portions respectively in mutually diverging first and second directions; likewise the third and fourth straight tapered portions extend from the first and second radiused portions respectively in mutually diverging third and fourth directions. A taper angle between the first straight tapered portion and an intersecting line parallel to the vertical axis is in a range of 1 to 10 degrees inclusive.

A further aspect is a test coupon assembly comprising: a test coupon made of fiber-reinforced plastic material of constant thickness, the test coupon comprising first and second trapezoidal portions connected by a gauge area having a coupon minimum width, the first and second trapezoidal portions and the gauge area forming respective portions of a front face and respective portions of a rear face of the test coupon, each of the front and rear faces having a bow-tie-shaped profile; first and second tabs adhered to the first trapezoidal portion on respective first portions of the front and rear faces; and third and fourth tabs adhered to the second trapezoidal portion on respective second portions of the front and rear faces. Each of the first through fourth tabs is made of fiber-reinforced plastic material and has a trapezoidal profile.

In accordance with one embodiment of this further aspect, the first trapezoidal portion comprises first and second straight tapered sides, the second trapezoidal portion comprises third and fourth straight tapered sides, and the gauge area comprises first and second radiused sides. The test coupon has a minimum width in the gauge area and a constant thickness, the first radiused side being connected to the first and third straight tapered sides, and the second radiused side being connected to the second and fourth straight tapered sides. The height of the gauge area is no greater than 3% of a height of the test coupon, and a taper angle between the first straight tapered portion and an intersecting line parallel to the vertical axis is in a range of 1 to 10 degrees inclusive.

Other aspects are disclosed and claimed below.

BRIEF DESCRIPTION OF THE DRAWINGS

Various embodiments will be hereinafter described with reference to drawings for the purpose of illustrating the foregoing and other aspects.

Reference will hereinafter be made to the drawings in which similar elements in different drawings bear the same reference numerals.

DETAILED DESCRIPTION

The test coupon geometries disclosed herein have particular application in the field of fatigue testing of scratched composite coupons. Composite scratch testing is conducted to determine the adverse effect of various scratch depths on a composite coupon comprising a layup of multiple plies, each ply comprising fiber-reinforced plastic. The fiber directions in adjacent plies are varied to provide increased strength and stiffness in the final laminate. The composite layup coupons can be cut using a water jet programmed according to the desired coupon geometry. Each coupon comprises first and second load application regions at opposing ends of the coupon, where tabs will be bonded, and a relatively narrower central section (hereinafter "gauge area") of reduced cross section, which feature is designed to promote failure at the center of the coupon. Each load application region will have a pair of tabs bonded on both sides thereof. The tabs facilitate the application of test loads to the coupon by a test machine.

One implementation of composite scratch testing calls for fatigue testing of both pristine coupons and coupons with a scratch introduced across the gauge area. The S-N curves of the pristine coupons and the scratched coupons will then be compared to determine the material strength reduction due to the scratches. In a search for a suitable coupon geometry, it has been discovered that a bow-tie-shaped coupon has improved performance during fatigue testing. The bow-tie shape induces a slight stress concentration at the gauge area, causing the coupons to reliably fail at that location in low- and high-cycle fatigue without affecting the S-N curve shape. Using this coupon geometry, scratches can be inflicted across the gauge area to provide for reliable comparisons between the unscratched and scratched coupons.

Figure 1A:
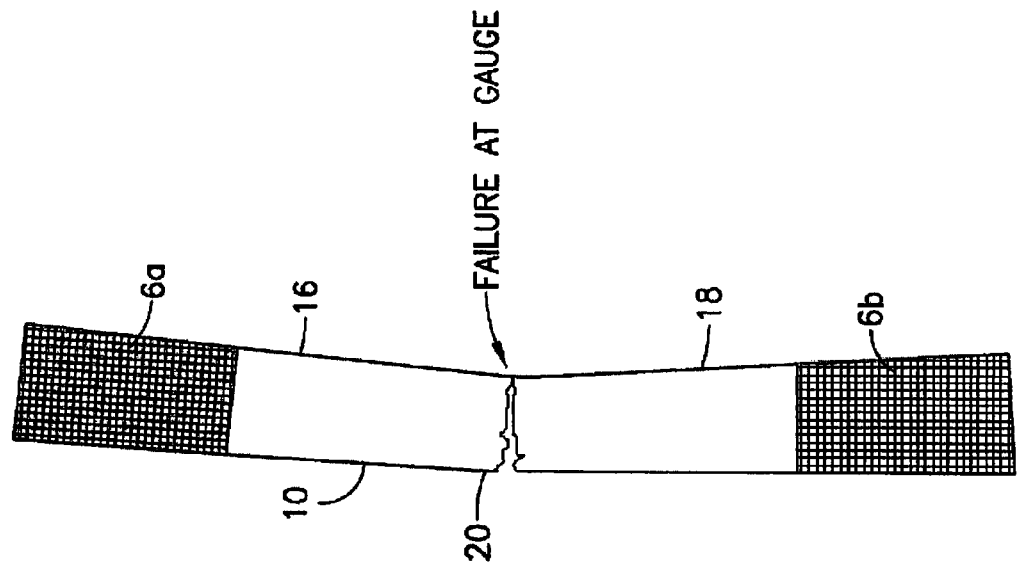
FIG. 1A is a diagram showing a top view of a rectangular composite test coupon that has failed at the tabs.
Figure 1B:
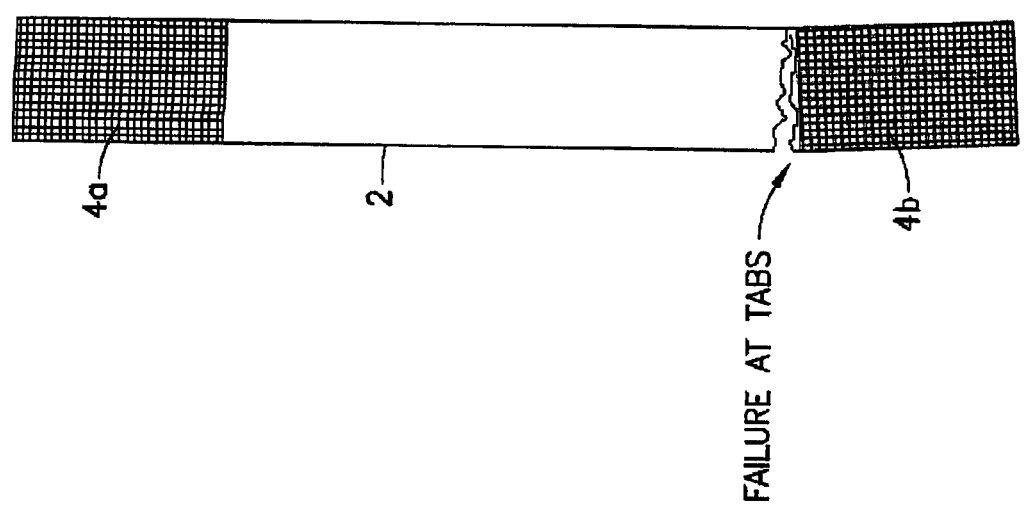
FIG. 1B is a diagram showing a top view of a composite test coupon with tapered sides that has failed at the gauge section.

The improved performance of a bow-tie-shaped composite test coupon with similarly shaped tabs as compared to a rectangular composite test coupon with rectangular tabs can be seen in FIGS. 1A and 1B.

FIG. 1A shows a top view of a rectangular test coupon 2 that has failed at the tabs. The front face of the test coupon 2 seen in FIG. 1 is rectangular. This test coupon has rectangular tabs adhered to the front and rear faces near both ends of the coupon. Only tabs 4a and 4b, adhered to the front face of coupon 2, are visible in FIG. 1A. As seen in FIG. 1A, failure of the coupon 2 has occurred near tab 4b.

In contrast, FIG. 1B shows a top view of a composite test coupon 10 with tapered sides that has failed at the gauge section 20. This coupon was constructed such that loads were applied parallel with the laminations and are in-plane with the plies. In an undeformed state, test coupon 10 had a bow-tie-shaped profile and comprised upper and lower trapezoidal portions 16 and 18 connected to the gauge area 20. Each trapezoidal portion 16, 18 had straight divergent tapers on both sides of the coupon. Similarly shaped (i.e., trapezoidal) tabs, designed to receive the test load, were adhered to the front and rear faces near both ends of the coupon. The undeformed test coupon also had a constant thickness, the thickness direction being normal to the planes in which the composite plies lie. Only tabs 6a and 6b, adhered to the front face of coupon 10, are visible in FIG. 1B.

The particular test coupon depicted in FIG. 1B had an original bow-tie-shaped geometry with specific dimensions. However, it should be appreciated that the test coupon geometry disclosed herein is not limited to a single dimension set, but rather encompasses bow-tie-shaped geometries having dimensions which fall within respective ranges. In particular, the taper angle on the sides of the coupon may be varied in the range from 1 to 10 degrees.

Figures 2, 2A:
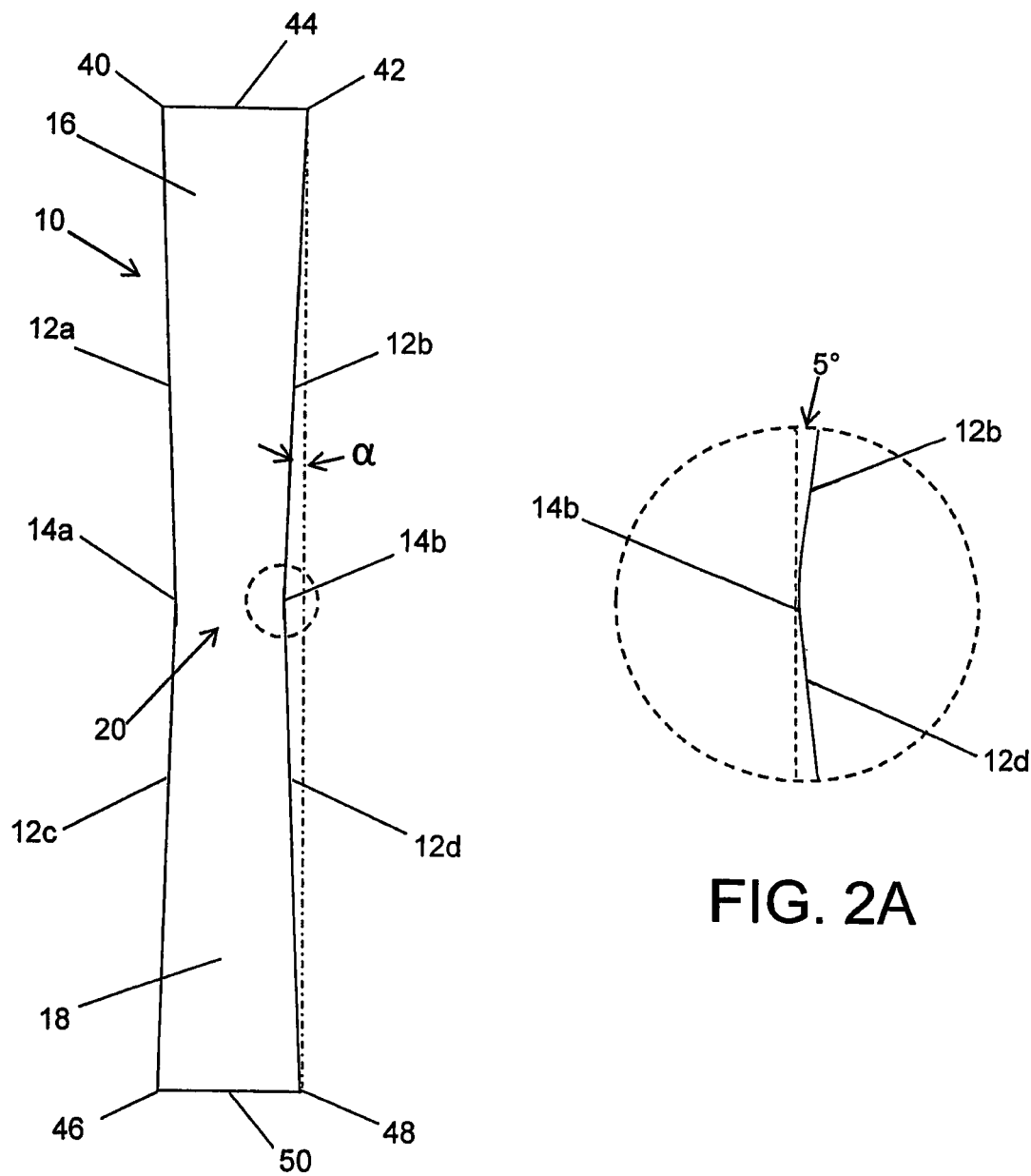
FIG. 2 is a diagram showing a top view of a composite test coupon geometry in which the taper angle α is in the range of 1 to 10 degrees.
FIG. 2A is a diagram showing a magnified view of the area inside the dashed circle in FIG. 2

FIG. 2 shows the two-dimensional geometry of a bow-tie-shaped test coupon 10 without tabs, not drawn to scale. Because the coupon is not drawn to scale in FIG. 2, the intent of this drawing is to depict a taper angle α that may have any magnitude in the aforementioned range of 1 to 10 degrees. In the undeformed state, the test coupon 10 comprises three regions: a first trapezoidal portion 16 having first and second straight tapered sides 12a and 12b; a second trapezoidal portion 18 having third and fourth straight tapered sides 12c and 12d; and a gauge area 20 having first and second radiused sides 14a and 14b. The first and second radiused sides 14a and 14b of the gauge area 20 are concave, so that the minimum width of the test coupon occurs along a line connecting the midpoints of the first and second radiused sides 14a and 14b. The dot-dash vertical line in FIG. 2 indicates where the right side of the coupon would be if the front face of the test coupon were rectangular instead of bow-tie-shaped.

The second radiused side 14b is connected to the second straight tapered side 12b and to the fourth straight tapered side 12d, as shown better in FIG. 2A, which is a magnified view of the area inside the dashed circle in FIG. 2. Similarly, the first radiused side 14a is connected to the first straight tapered side 12a and to the third straight tapered side 12c. The test coupon 10 has a bow-tie-shaped profile from its front face, as shown in FIG. 2, to its rear face and has a constant thickness (i.e., the distance between the front and rear faces is constant). Preferably, the taper angles for all tapered sides 12a through 12d are equal. Likewise the radii of the radiused sides 14a and 14b are the same and their arc lengths are also the same. The first and third straight tapered sides 12a and 12c may be tangent to the first radiused side 14a of gauge area 20, while the second and fourth straight tapered sides 12b and 12d may be tangent to the second radiused side 14b of gauge area 20.

Alternatively, the composite test coupon 10 can be characterized as having a constant thickness, a height along a vertical axis, and a bow-tie-shaped profile when viewed along an axis in a thickness direction. The bow-tie-shaped profile comprises left and right sides and top and bottom ends 44 and 50. The left side comprises a first radiused portion 14a and first and third straight tapered portions 12a and 12c extending from the first radiused portion 14a toward the top and bottom ends 44 and 50 respectively; the right side comprises a second radiused portion 14b and second and fourth straight tapered portions 12b and 12d extending from the second radiused portion 14b toward the top and bottom ends 44 and 50 respectively. The first and second straight tapered portions 12a and 12b extend from the first and second radiused portions 14a and 14b respectively in mutually diverging first and second directions; the third and fourth straight tapered portions 12c and 12d extend from the first and second radiused portions 14a and 14b respectively in mutually diverging third and fourth directions. The taper angle between the first straight tapered portion 12a and an intersecting line parallel to the vertical axis is in a range of 1 to 10 degrees inclusive. The taper angles of the other straight tapered portions may be equal to the taper angle of the first straight tapered portion 12a.

As seen in FIG. 2, the first straight tapered portion 12a may be connected to the top end 44 of the coupon at a first corner 40; the second straight tapered portion 12b may be connected to the top end 44 at a second corner 42; the third straight tapered portion 12c may be connected to the bottom end 50 of the coupon at a third corner 46; and the fourth straight tapered portion 12d may be connected to the bottom end 50 at a fourth corner 48. In the alternative, the corners 40, 42, 46 and 48 may be rounded or beveled. For purposes of this disclosure, the shape formed by straight tapered sides 12a and 12b, top end 44 and a hypothetical straight line connecting the upper end points of the arcs of each radiused portion 14a and 14b will be deemed "trapezoidal" even though the corners at the top have been rounded or beveled. The same is true for the lower half of the test coupon.

For the embodiments disclosed herein, the height of the gauge area 20 (i.e., the distance separating the endpoints of the arc of each radiused portion 14a and 14b) is preferably no greater than 3% of the height of the composite test coupon 10 (measured from the top end 44 to the bottom end 50).

In accordance with one proposed embodiment, a test coupon was designed having the following dimensions: height, 9.000 inches; end width, 1.340 inches; gauge width, 1.000 inch; gauge radius, 0.080 inch; and taper angle $\alpha=2.163°$. As previously mentioned, the taper angle may vary within the range of 1 to 10 degrees.

It is predicted that test coupons designed in accordance with the above-described geometry and having taper angles within the aforementioned range will reliably fail at the gauge section without affecting the material (i.e., S-N) curve shape.

Figure 3A:
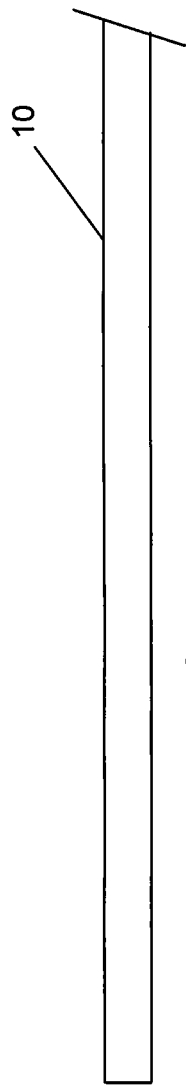
FIG. 3A is a diagram showing one end of a test coupon without tabs.

FIG. 3A shows one end of a test coupon 10 without tabs. Sometimes coupons without tabs are tested as it is not an ASTM requirement. The test coupon 10 shown in FIG. 3A has a constant thickness.

In the alternative, different tab geometries may be employed in conjunction with test coupon geometry shown in FIG. 2. Preferably, the tabs have a trapezoidal profile similar to the profile of that portion of the bow-tie-shaped test coupon to which the tabs are adhered.

Figure 3B:
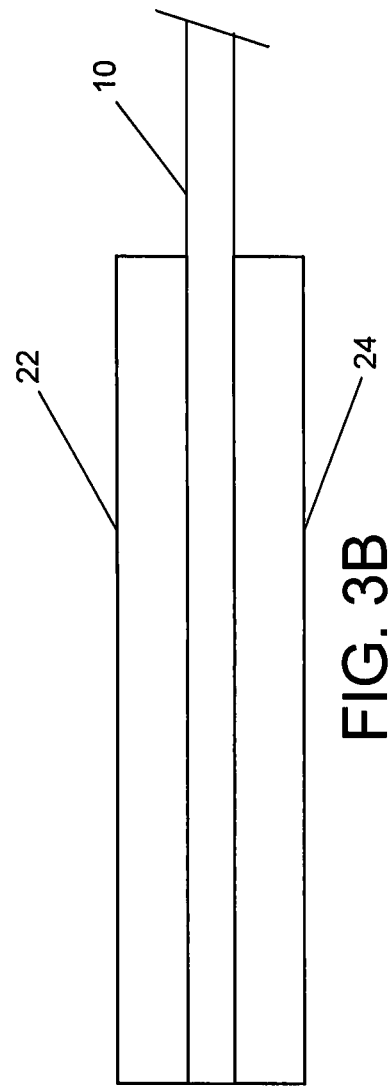
FIG. 3B is a diagram showing one end of a test coupon having unbeveled tabs adhered to the front and back of the coupon.

FIG. 3B shows one end of a bow-tie-shaped test coupon 10 having unbeveled tabs 22 and 24 adhered to the front and rear faces of the test coupon. Although not visible in FIG. 3B, tabs 22 and 24 have trapezoidal front faces.

Figure 3C:
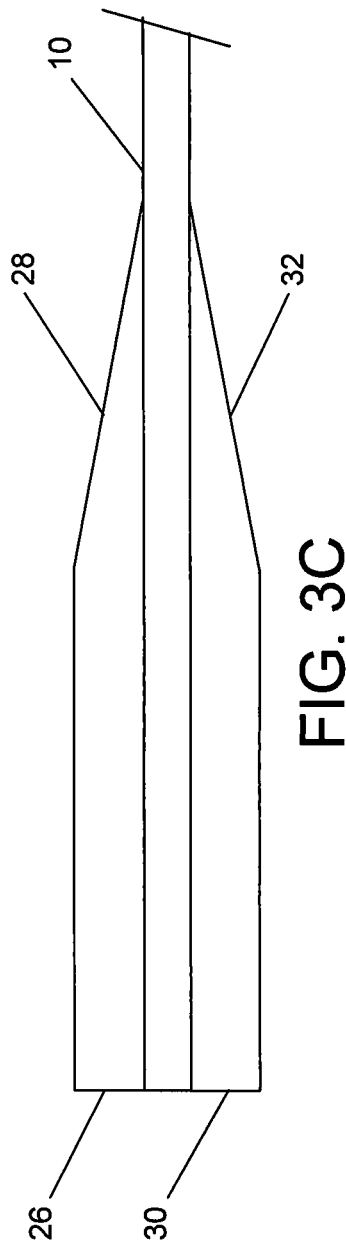
FIG. 3C is a diagram showing one end of a test coupon having beveled tabs adhered to the front and back of the coupon.

FIG. 3C shows one end of a bow-tie-shaped test coupon 10 having beveled tabs 26 and 30 adhered to the front and rear faces of the test coupon. Although not visible in FIG. 3C, tabs 26 and 30 have a trapezoidal profile when viewed from the front. In this implementation, tab 26 comprises a beveled surface 28, while tab 30 comprises a beveled surface 32. The beveling lowers stress concentration at the tab ends.

FIGS. 3B and 3C show portions of respective test coupon assemblies. Each test coupon assembly comprises: a test coupon 10 made of fiber-reinforced plastic material of constant thickness, the test coupon comprising first and second trapezoidal portions (items 16 and 18 in FIG. 2) connected by a gauge area (item 20 in FIG. 2) having a coupon minimum width. The first and second trapezoidal portions and the gauge area form respective portions of a front face and respective portions of a rear face of the test coupon, each of the front and rear faces having a bow-tie-shaped profile. The test coupon assembly further comprises first and second tabs adhered to the first trapezoidal portion on respective first portions of the front and rear faces of the coupon; and third and fourth tabs adhered to the second trapezoidal portion on respective second portions of the front and rear faces of the coupon. Each of the four tabs is made of fiber-reinforced plastic material and has a trapezoidal profile.

The above-described bow-tie-shaped geometry produces a gradual stress transition between the test machine, tabs and coupon. On both sides of the coupon, the tapers culminate in the gauge area, which becomes the highest stressed portion of the coupon during fatigue testing. However, unlike open-hole coupons that induce failure in the gauge area, this coupon geometry does not change the shape of the material S-N curve and maintains a nominal gauge width. Moreover, the proposed test coupons preferably have attached tabs shaped to follow the profile of the bow-tie-shaped coupon; this solves the problem that previous "dogbone" coupon attempts have faced, namely, that the failure point occurs at the start of the dogbone region rather than in the gauge area.

While composite coupon geometries have been described with reference to various embodiments, it will be understood by those skilled in the art that various changes may be made and equivalents may be substituted for elements thereof without departing from the scope of the invention. In addition, many modifications may be made to adapt a particular situation to the teachings herein without departing from the essential scope thereof. Therefore it is intended that the claims not be limited to the particular embodiments disclosed.

As used in the claims, the term "trapezoidal portion" should be construed broadly to encompass trapezoid-shaped portions of a test coupon which have two straight tapered sides and one straight end, but are integrally formed with a gauge area on a fourth side of the trapezoid. The straight tapered sides may connect to the straight end at respective corners or the test coupon may have rounded corners which are connected to the straight end and a respective straight tapered side.

The invention claimed is:

1. A test coupon assembly comprising:
a test coupon comprising a multiplicity of plies made of fiber-reinforced plastic material laminated together to form a laminate of constant thickness, said test coupon having a geometry comprising first and second trapezoidal portions connected by a gauge area having a coupon minimum width, said first and second trapezoidal portions and said gauge area forming respective portions of a front face and respective portions of a rear face of the test coupon, each of said front and rear faces having a bow-tie-shaped profile and being parallel to said plies;
first and second tabs adhered to said first trapezoidal portion on respective first portions of said front and rear faces; and
third and fourth tabs adhered to said second trapezoidal portion on respective second portions of said front and rear faces,
wherein each of said first through fourth tabs is made of fiber-reinforced plastic material, each of said first through fourth tabs has a trapezoidal profile, said test coupon has a minimum width in said gauge area and a constant thickness, said first trapezoidal portion comprises first and second straight tapered sides, said second trapezoidal portion comprises third and fourth straight tapered sides, said gauge area comprises first and second radiused sides, said first radiused side is connected to said first and third straight tapered sides, said second radiused side is connected to said second and fourth straight tapered sides, and a height of said first radiused portion is no greater than 3% of a height of the test coupon.

2. The test coupon assembly as recited in claim 1, wherein said first and second straight tapered sides diverge from each other and said third and fourth straight tapered sides diverge from each other as said first through fourth straight tapered sides extend away from said gauge area.

3. The test coupon assembly as recited in claim 1, wherein said first and third straight tapered sides are tangent to said first radiused side of said gauge area at respective intersection points of said first and third straight tapered sides with said first radiused side, and said second and fourth straight tapered sides are tangent to said second radiused side of said gauge area at respective intersection points of said second and fourth straight tapered sides with said second radiused side.

4. The test coupon assembly as recited in claim 1, wherein taper angles of said first through fourth straight tapered sides are equal.

5. The test coupon assembly as recited in claim 4, wherein the taper angle is in a range of 1 to 10 degrees inclusive.

6. The test coupon assembly as recited in claim 1, wherein radii of said first and second radiused sides are equal.

\* \* \* \* \*